United States Patent [19]

Su

[11] Patent Number: 6,163,717
[45] Date of Patent: Dec. 19, 2000

[54] OPEN STRUCTURE BREAST COIL AND SUPPORT ARRANGEMENT FOR INTERVENTIONAL MRI

[75] Inventor: Sunyu Su, South San Francisco, Calif.

[73] Assignee: Toshiba America MRI, Inc., Tustin, Calif.

[21] Appl. No.: 09/198,967

[22] Filed: Nov. 25, 1998

[51] Int. Cl.[7] .................................................. A61B 5/055
[52] U.S. Cl. .......................................... 600/422; 324/318
[58] Field of Search .................................. 600/411, 422; 606/130; 324/318, 322

[56] References Cited

U.S. PATENT DOCUMENTS

| | | | |
|---|---|---|---|
| 4,534,358 | 8/1985 | Young | 600/422 |
| 5,024,229 | 6/1991 | Bryant et al. | 600/422 |
| 5,129,911 | 7/1992 | Siczek et al. | 606/130 |
| 5,357,958 | 10/1994 | Kaufman | 600/411 |
| 5,363,845 | 11/1994 | Chowdhury et al. | 600/422 |
| 5,386,191 | 1/1995 | McCarten et al. | 324/318 |
| 5,386,447 | 1/1995 | Siczek | 378/37 |
| 5,416,413 | 5/1995 | Leussler | 324/318 |
| 5,437,280 | 8/1995 | Hussman . | |
| 5,500,594 | 3/1996 | Leussler | 324/318 |
| 5,515,855 | 5/1996 | Meyer et al. | 600/422 |
| 5,517,120 | 5/1996 | Misic et al. | 324/318 |
| 5,534,778 | 7/1996 | Loos et al. | 324/318 |
| 5,565,780 | 10/1996 | Derby | 324/322 |
| 5,569,266 | 10/1996 | Siczek | 606/130 |
| 5,592,088 | 1/1997 | Matsunaga et al. | 324/318 |
| 5,595,177 | 1/1997 | Mena et al. . | |
| 5,602,479 | 2/1997 | Srinivasan et al. | 324/318 |
| 5,602,557 | 2/1997 | Boskamp | 324/318 |
| 5,696,449 | 12/1997 | Duerr | 324/318 |
| 5,699,802 | 12/1997 | Duerr | 600/422 |
| 5,702,405 | 12/1997 | Heywang-Koebrunner | 606/130 |
| 5,706,812 | 1/1998 | Strenk et al. | 600/422 |
| 5,804,969 | 9/1998 | Lian et al. | 324/318 |
| 6,023,166 | 2/2000 | Eydelman | 324/318 |

OTHER PUBLICATIONS

Chen, C.-N. et al., "Quadrature Detection Coils—A Further √2 Improvement in Sensitivity", Journal of Magnetic Resonance 54, 1983, pp. 324–327.

Daniel, B.L. et al., "Interactive MR-Guided, 14-Gauge Core-Needle Biopsy of Enhancing Lesions in a Breast Phantom Mode", Acad Radiol, vol. 4, No. 7, Jul. 1997, pp. 508–512.

Fischer, Uwe, MD et al., "MR-Guided Biopsy of Suspect Breast Lesions with a Simple Stereotaxic Add-On Device for Surface Coils", Radiology, vol. 192, No. 1, Jul. 1994, pp. 272–273.

Fischer, Uwe, MD et al., "MR Imaging-Guided Breast Intervention: Experience with Two Systems", Radiology, vol. 195, May 1995, pp. 533–538.

(List continued on next page.)

*Primary Examiner*—Ruth S. Smith
*Attorney, Agent, or Firm*—Nixon & Vanderhye P.C.

[57] ABSTRACT

A pair of RF quadrature detection coils are fitted in an open support structure that allows easy diagnostic access to all tissue areas of the human female breast when performing interventional MRI. The open structure dual coil arrangement comprises a flat base and a slightly "V"-shaped bi-planar upper section supported above the lower base section by eight narrow vertical legs. The upper bi-planar section includes two circular openings for accepting the breasts. Four of the support legs are equally spaced at 900 intervals around each breast opening and provide large side-open access areas to the breast tissues via the sides of the support structure. The "V"-shape of the upper portion of the coil support structure increases the gap clearance at both left and right sides of the support structure to further enhance access to the breasts. In a preferred embodiment, two complete MRI quadrature detection coils are supported by the structure and each of the vertical support legs house a pair of conductors forming part of a quadrature detection coil winding. The use of quadrature detection coils increases MRI signal detection efficiency and the open structural support arrangement allows increased accessibility to the breast tissues for efficient interventional MR imaging and easy cleaning after use.

10 Claims, 3 Drawing Sheets

OTHER PUBLICATIONS

Gould, Stuart W.T. et al., "Interventional MR–Guided Excisional Biopsy of Breast Lesions", Journal of Magn Reson Imaging, vol. 8, No. 1, Jan./Feb. 1998, pp. 26–30.

Harms, Steven E. et al., "Magnetic Resonance Imaging of the Breast", Magnetic Resonance Quarterly, vol. 8, No. 3, Sep. 1992, pp. 139–155.

Heywang–Köbrunner, Sylvia H. et al., "Prototype Breast Coil for MR–Guided Needle Localization", Journal of Computer Assisted Tomography, vol. 18, No. 6, Nov./Dec. 1994, pp. 876–881.

Hoult, D. I. et al., "Quadrature Detection in the Laboratory Frame", Magnetic Resonance in Medicine vol. 1, Sep. 1984, pp. 339–353.

Hyde, James S., "Quadrature Detection Surface Coil", Magnetic Resonance in Medicine, vol. 4, Feb. 1987, pp. 179–184.

Kandarpa, K. et al., "Prototype Miniature Endoluminal MR Imaging Catheter", J Vasc Interv Radiol, vol. 4, No. 3, May 1993, pp. 419–427.

Muller–Schimpfle, M. et al., "Precise MR–Guided Preoperative Marking of Breast Lesions with an Embolization Coil Using a Standard MR Coil", Rofo Fortschr Geb Rontgenstr Neuen Bildgeb Verfahr, vol. 168, No. 2, Feb. 1998, pp. 195–199.

Orel, Susan G., MD et al., "MR Imaging–Guided Localization and Biopsy of Breast Lesions: Initial Experience", Radiology, vol. 193, No. 1, Oct.1994, pp. 97–102.

Redpath, Thomas W., "Quadrature rf Coil Pairs", Magnetic Resonance in Medicine, vol. 3, 1986, pp. 118–119.

Schenck, John F. et al., "Superconducting Open–Configuration MR Imaging System for Image–Guided Therapy", Radiology, vol. 195, Jun. 1995, pp. 805–814.

OPEN STRUCTURE BREAST COIL AND SUPPORT ARRANGEMENT FOR INTERVENTIONAL MRI

CROSS-REFERENCE TO RELATED APPLICATIONS

This application is related to commonly-assigned co-pending U.S. application Ser. No. 09/199,411 to Sunyu Su, entitled "Quadrature Detection Coil For Interventional MRI", filed Nov. 25, 1998, the disclosure of which is incorporated by reference in its entirety.

FIELD OF THE INVENTION

This invention relates to open structure RF receive coils and an associated support structure for magnetic resonance imaging (MRI). More specifically, it relates to a quadrature type receive coils and associated support structures for obtaining MR images of the human breast which allows ample access to the breast tissues for permitting interventional MRI procedures.

BACKGROUND OF THE INVENTION

Magnetic resonance (MR) images acquired during surgery can assist a surgeon to accurately locate tissue malignancies, obtain a biopsy from desired locations and ensure successful tissue removal. Interventional MRI is the magnetic resonance imaging technique (often involving real-time imaging) that allows a surgeon to perform MRI-guided tissue biopsy or surgery. One application of interventional MRI is to guide a surgeon during a biopsy or surgical operation on one or both of the breasts of female patients Interventional MRI procedures typically require that an MR signal detection coil have large openings so that a surgeon can have access to the surgical site through the coil with biopsy needle or other surgical devices. The need for surgical access through an MR signal detection coil is a significant constraint on the design of the coil. To meet the tissue accessibility requirements of interventional MRI procedures, conventional MRI breast coils are often single-channel simple coil windings having a structural configuration that limits coil performance.

One such example of a simplified breast coil configuration used in MRI is a conventional flat single-loop surface coil. This type of breast coil is typically placed around a breast near the chest wall of the patient. A major disadvantage of the simplified breast coil is that it has very poor field homogeneity. In other words, it provides very poor received signal quality from any tissue that is far away from the loop. Because of these disadvantages, for example, a surgeon may not be able to positively identify or remove malignancies at certain regions of the breast, especially in tissue that is removed from the breast coil.

The signal detection efficiency of a MRI detection coil is important to providing useable tissue images. A higher signal detection efficiency means a better quality signal and a cleaner image which allows a surgeon to see the subject tissues more clearly and make correct decisions regarding the imaged tissues. In this regard, it is known that an RF quadrature type detection coil can provide a much improved signal detection efficiency over the simple single channel coil typically used for interventional MRI surgical procedures.

In interventional MRI it is crucial that an RF reception coil produce high quality, low noise MR signals that will result in good quality high resolution images so that a surgeon can accurately identify, locate and access the desired tissues. A competing requirement for interventional MRI detection coils is that they allow surgical access to the surgical site. The difficulty in providing surgical access is especially difficult for breasts, due to their sizes and shapes. The compromised performance of conventional MRI breast coil arrangements may lead to poor imaging and hence false diagnosis or imprecise surgery. In accordance with the present invention, a novel MRI breast coil and support arrangement is provided that utilizes a highly efficiency quadrature type detection coil arrangement and has an open structure for allowing maximum access to imaged tissues.

SUMMARY OF THE INVENTION

The present invention is directed to a dual receive coil and support structure arrangement for interventional MRI that is capable of simultaneously accepting two human female breasts. A pair of RF quadrature detection coils are fitted in an open support structure that allows easy diagnostic and surgical access to tissue areas when performing interventional MRI procedures (e.g., tissue biopsy or surgery during imaging).

In accordance with the present invention, an MRI breast coil support structure comprises a flat base and a bi-planar upper portion supported above the lower base portion by narrow vertical legs that provide large between-plane openings for easy surgical access to the breasts by a biopsy needle or other diagnostic instruments. The upper portion is slightly "V"-shaped (bi-planar) and includes two circular openings for accepting the breasts. The slight "V"-shape of the bi-planar upper portion increases the clearance at both left and right sides of the coil support structure to further enhance accessibility to the breasts from the sides. Eight vertical support legs—four equally spaced at 90° intervals around each breast opening—provide large open access areas to the breast tissues via the sides of the coil support structure. In a preferred embodiment of the present invention, two complete pairs of MRI quadrature detection coils are supported by the structure. Each of the vertical support legs house a pair of conductors to form a portion of a quadrature detection coil winding. In particular, the four support legs house the four legs of a quadrature-detection coil for each breast.

The open structure coil support structure of the present invention, comprising a "V"-shaped top plane, flat bottom plane and eight connecting legs altogether, is easily fitted with either a conventional detection coil or a high efficiency quadrature type receive coil, and allows increased accessibility to the breast tissues for efficient interventional MR imaging. In addition, the open structure of the present invention allows for easy cleaning after use.

Accordingly, one embodiment of the invention is a magnetic resonance imaging (MRI) quadrature detection coil and support structure comprising:
  a lower surface;
  an upper surface having an aperture to receive a body part;
  four legs connecting the upper and lower surfaces, wherein the four legs are arranged around the aperture;
  an RF quadrature detection coil having conductor windings circumferentially around the aperture in the upper surface and conductor windings in each of the four legs, and
  an open gap between the upper and lower surfaces to allow access through the coil and support structure to the body part.

Another embodiment of the invention is a dual magnetic resonance imaging (MRI) quadrature detection coil and support structure arrangement, comprising:

a bottom portion;

an upper portion comprising first and second upper sections, where each section has an aperture to receive a breast;

eight leg portions connecting said top and bottom portions, wherein four leg portions are arranged around each aperture;

a first RF quadrature detection coil having conductor winding portions positioned circumferencially about the aperture in the first upper section and conductor winding portions in each of four leg portions disposed around the aperture in the first upper section; and a second RF quadrature detection coil having conductor winding portions positioned circumferencially about the aperture in the second upper section and conductor winding portions in each of four leg portions disposed around the aperture in the second upper section.

A further embodiment of the invention is a magnetic resonance imaging RF coil support structure, comprising:

a flat-planar bottom portion;

a bi-planar v-shaped upper portion comprising first and second planar sections each section having a large circular opening;

eight leg portions connecting said top and bottom portions, wherein each leg portion is disposed perpendicular to said bottom portion and four leg portions are arranged around each opening at substantially equal 90° intervals; and a base support housing portion.

BRIEF DESCRIPTION OF THE DRAWINGS

The purpose and advantages gained by the present invention will be understood by careful study of the following detailed description of the presently preferred embodiment with particular reference to the accompanying drawings, wherein.

DETAILED DESCRIPTION OF THE PRESENTLY PREFERRED EMBODIMENT

Figure 1:
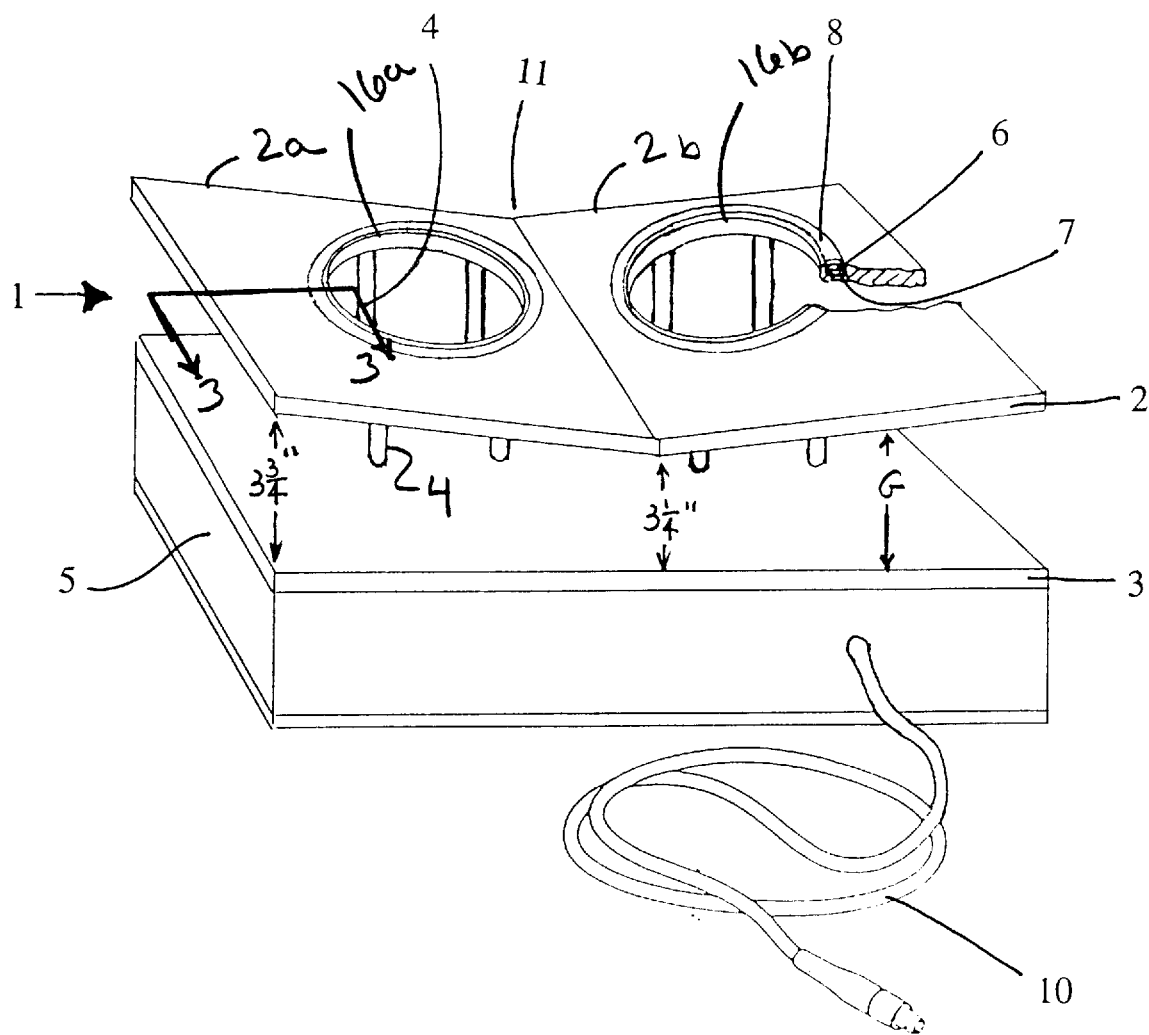
FIG. 1 is a perspective view of a dual quadrature detection coil device and support structure arrangement for magnetic resonance imaging of the female breasts in accordance with the present invention.

FIG. 1 shows a perspective view of a dual breast MRI receive coil support structure 1 comprising a "V"-shaped upper bi-planar portion 2, a bottom flat planar section 3, eight vertical leg portions 4 between the upper and bottom planar sections, and a base housing portion 5, below the bottom planar section.

The planar upper section 2 comprises left and right planar sections 2a, 2b that are mirror symmetrical along center line 11. The slight "V"-shape of the bi-planar upper section increases the clearance between the upper and bottom sections at both left and right sides of the coil support structure 1 to enhance accessibility to the breasts from these sides.

Each of the left and right upper planar sections 2a, 2b has a large central circular opening 16a, 16b for accepting a breast. Surrounding the circular opening in each upper section, a shallow groove 6 is provided on the top surface for housing conductors which form a portion of a supported MR signal detection coil. The groove 6 is fitted in the rim of the openings 16a, 16b of a double-sided printed circuit (PC) board 7 that contains printed circuit conductor portions of a quadrature type receive coil winding.

Figure 3:
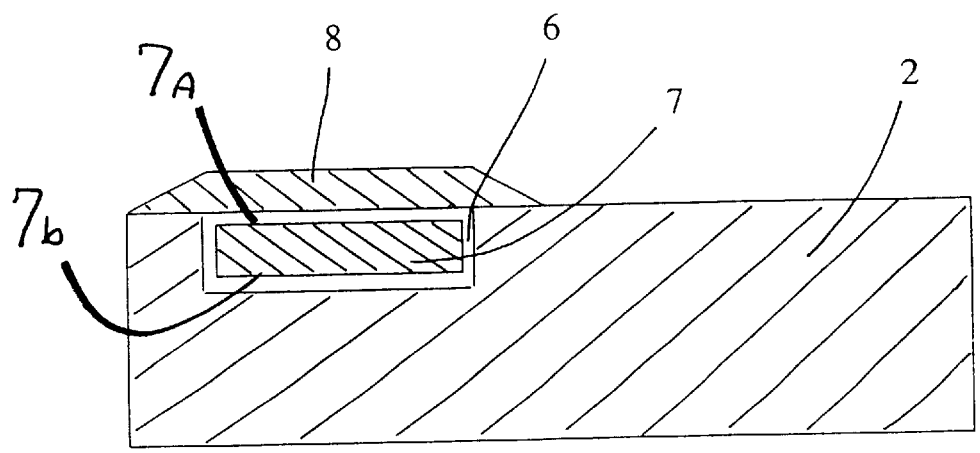
FIG. 3 is an enlarged drawing showing detail of cross section taken along 3—3 of FIG. 1 of the groove, the inserted ring-shaped PC board and protective covering piece.

Covering groove 6 is a thin electrically-insulating ring-shape protective shield 8 that is closely fitted to seal the groove against moisture and fluids. An enlarged drawing of the shield 8 is shown in FIG. 3. The shield 8 may be formed of a plastic material that does not interfere with or diminish RF signals. In addition, the doubled-sided PC board 7 may be an annular ring having conductive coil windings mounted on circumferential interior 7a and exterior 7b surfaces of the board, or be an annular disk having conductive coil windings on upper and lower sides of the PC board, as is shown in Ser. No. 09/199,411 to Sunyu Su, entitled "Quadrature Detection Coil For Interventional MRI", (attny. dkt. 202-76), which is incorporated by reference.

Sufficient clearance is provided between the bi-planar upper section 2 and flat bottom support section 3 to allow easy access to all tissues of the breast when performing interventional MRI. For example, a construction having a gap (G) sloping from 3¼" at the center line 11 and outward to 3¾" the left and right sides of the support structure 1. The sloping side gaps allow adequate access in most instances for the insertion of a biopsy needle. Larger opening spaces are also possible, to the extent that the vertical dimension of MRI magnet permits. Upper and lower sections 2 and 3 are rigidly connected to each other by eight vertical legs 4. Four legs are positioned around each breast opening 16a, 16b. The four legs are spaced at equal 90° intervals from each other around each opening.

Figure 2:
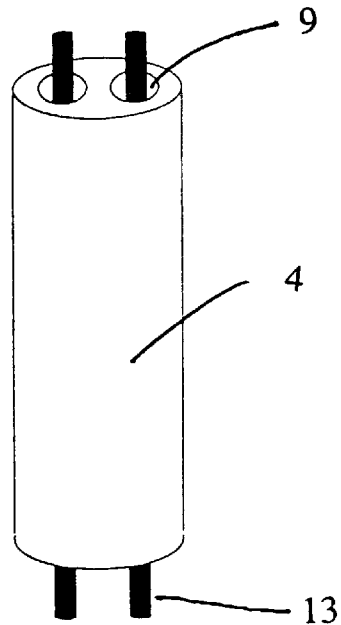
FIG. 2 is a descriptive drawing showing a portion of a leg of the support structure with two parallel longitudinal recesses housing a pair of vertical conductors of a coil winding.

Each leg is provided with two parallel longitudinal hollow recesses 9 (see FIG. 2) or, alternatively, may be a vertical slit for access to the leg's interior. These recesses 9 (or slits) allow for the insertion of a conductor coil winding portion 13 of a MR signal detection coil. The vertical coil winding portions housed within support structure legs 4 connect with a printed circuit conductor coil winding portions 7 on the annulus of the openings in the PC boards 7, and with other coil winding conductor portions (see FIG. 4, reference numeral 13) under bottom support plane 3 within base support housing 5. Additional longitudinal vertical recesses or openings may be provided in each leg to accommodate a more complex coil winding. In addition to serving as a housing for lower portions of MR signal detection coil windings, the base support 5 may also serve as a housing and storage compartment for other related MRI detection coil equipment such as LEMO cable 10 and/or, for example, a "tune-and-match" PC card.

Figure 4:
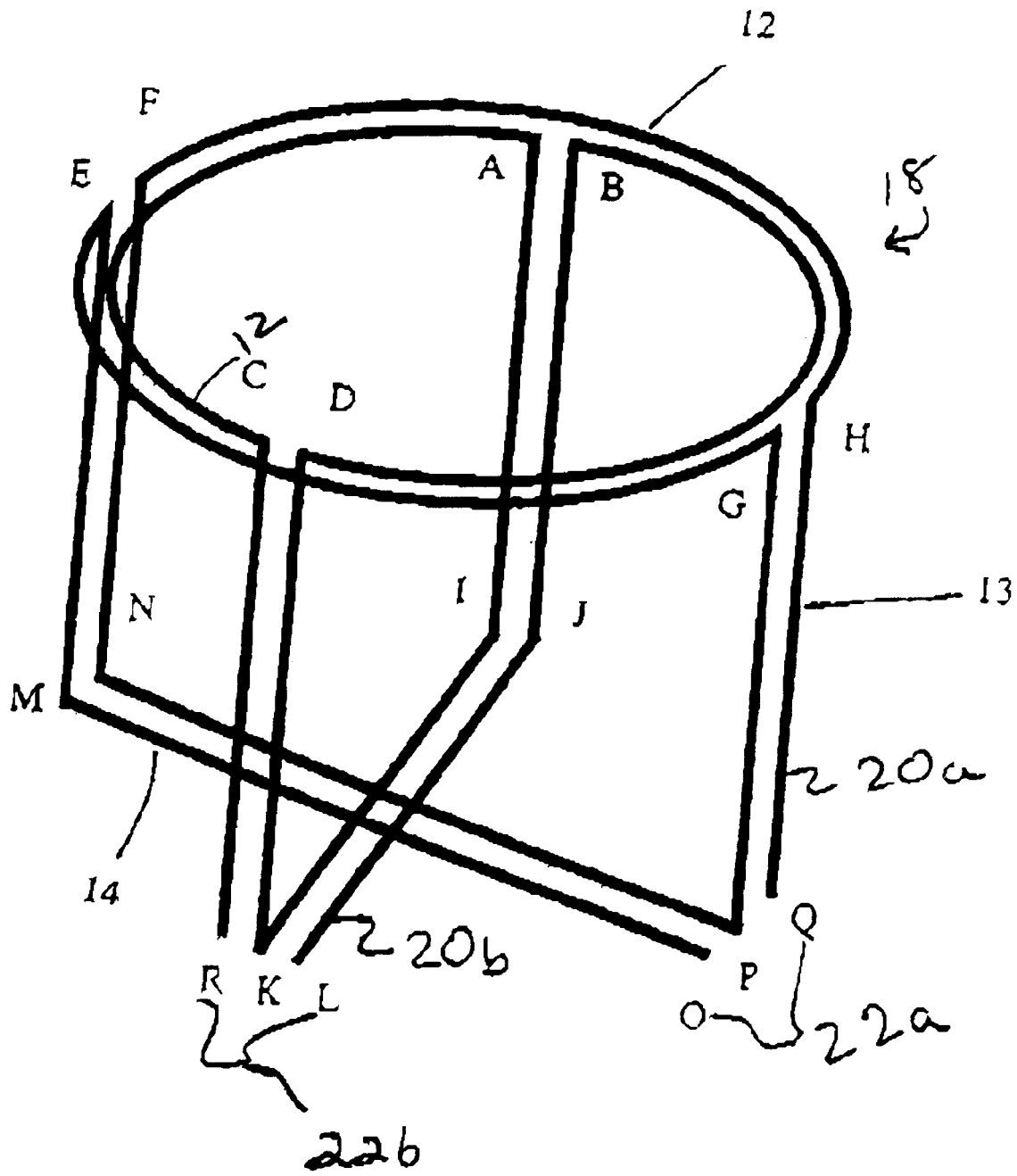
FIG. 4 is a schematic drawing of an RF quadrature reception coil for interventional MRI.

FIG. 4 shows schematically an RF quadrature signal detection coil 18, which are disclosed in more detail in application Ser. No. 09/199,411 which is incorporated by reference. The support structure 1 houses two of these quadrature signal detection coils 18. One quadrature detection coil fitted to each breast opening 16a, 1b, and its corresponding four support legs 4. Each quadrature coil comprises two individual MR receive coils 20a, 20b. Output lead connection points 22a, 22b are indicated at ends O-Q and R-L of the receive coils. Semicircular portions 12 (arcs F-H, E-G, B-D, A-C) of quadrature coil windings are printed on the ring-shaped PC board 7 Fitted into grooves 6 of upper support section 2. Vertical conductor portions of quadrature coil windings 13 are fitted to longitudinal recesses 9 in support structure legs 4. The bottom portions of quadrature coil windings 14 are housed in base housing 5 beneath the planar support bottom 3. Each quadrature coil 18 has its four output lead connection points 22a, 22b (O, Q, R, L) from the individual coil windings connected to conductors in a multi-conductor LEMO cable 10.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A dual magnetic resonance imaging (MRI) quadrature detection coil and support structure arrangement, comprising:
   a bottom portion;
   an upper portion comprising first and second upper sections, where each section has an aperture to receive a breast;
   eight leg portions connecting said top and bottom portions, wherein four leg portions are arranged around each aperture;
   a first RF quadrature detection coil having conductor winding portions positioned circumferentially about the aperture in the first upper section and conductor winding portions in each of four leg portions disposed around the aperture in the first upper section; and
   a second RF quadrature detection coil having conductor winding portions positioned circumferentially about the aperture in the second upper section and conductor winding portions in each of four leg portions disposed around the aperture in the second upper section.

2. A dual MRJ quadrature detection coil and support structure as set forth in claim 1 wherein said first and second upper sections each include a shallow circumferential groove on a top surface surrounding said aperture for accepting said conductor winding portions.

3. An RF detection coil support structure as set forth in claim 1, wherein said first and second upper sections each include a groove positioned circumferentially about the aperture and an electrically insulating ring-shaped groove cover for sealing the groove against entry of fluids and enclosing said detection coil conductor winding portions within the groove.

4. A dual MRI quadrature detection coil and support structure arrangement as set forth in claim 1 wherein a sloping clearance gap exists between both first and second upper sections and said bottom portion so as to provide access through the support structure to tissues of a breast inserted into the apertures in said first and second upper sections.

5. A dual magnetic resonance imaging (MRI) quadrature coil and support structure arrangement, comprising:
   a bottom portion;
   an upper portion comprising first and second upper sections, where each section has an aperture to receive a breast;
   eight leg portions connecting said top and bottom portions, wherein four leg portions are arranged around each aperture;
   a first RF quadrature detection coil having conductor winding portions positioned circuinferentially about the aperture in the first upper section and conductor winding portions in each of four leg portions disposed around the aperture in the first upper section;
   a second RF quadrature detection coil having conductor winding portions positioned circumferentially about the aperture in the second upper section and conductor winding portions in each of four leg portions disposed around the aperture in the second upper section, and
   bottom conductor winding portions coupled to the winding portions in each of the four leg portions, and said bottom conductor winding portions included within said bottom portion and connected to a cable passing through a side wall of said bottom portion.

6. A dual MRI quadrature detection coil and support structure arrangement as set forth in claim 5 wherein said bottom portion includes a printed circuit board containing circuitry for tuning coil tuning and matching.

7. A magnetic resonance imaging RF coil support structure, comprising:
   a planar bottom portion;
   a bi-planar v-shaped upper portion comprising first and second planar sections each section having a large opening;
   eight leg portions connecting said top and upper portions, wherein each leg portion is disposed perpendicular to said bottom portion and four leg portions are arranged around each opening at substantially equal 90° intervals;
   a pair of quadrature RF detection coils each having winding portions included within a periphery of said openings and winding portions included with each of the four leg portions arranged around the opening, and
   a base support housing portion.

8. An RF detection coil support structure as set forth in claim 7, wherein said large openings are each located substantially centrally within said first and second planar sections and are surrounded by a shallow circumferential groove for accepting said winding portions.

9. An RF receive coil support structure as set forth in claim 7, wherein a sloping clearance gap exists between both first and second sections of said bi-planar v-shaped upper portion and said planar bottom portion so as to provide easy access from all sides of the support structure to tissues of any body part inserted into the circular openings in said first and second planar sections.

10. A magnetic resonance imaging (MRI) quadrature detection coil and support structure comprising:
   a lower surface;
   an upper surface having an aperture to receive a body part;
   four legs connecting the upper and lower surfaces, wherein the four legs are arranged around the aperture;
   an RF quadrature detection coil having conductor windings circumferentially around the aperture in the upper surface and conductor windings in each of the four legs, and
   an open gap between the upper and lower surfaces to allow access through the coil and support structure to the body part.

* * * * *